(12) United States Patent
Schenk et al.

(10) Patent No.: US 8,765,365 B2
(45) Date of Patent: *Jul. 1, 2014

(54) SPERM CELL SEPARATION SYSTEM
(71) Applicant: XY, LLC, Navasota, TX (US)

(72) Inventors: John L. Schenk, Fort Collins, CO (US); George E. Seidel, Laporte, CO (US); Tae Kwang Suh, Fort Collins, CO (US)

(73) Assignee: XY, LLC, Navasota, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/953,372

(22) Filed: Jul. 29, 2013

(65) Prior Publication Data
US 2013/0309653 A1 Nov. 21, 2013

Related U.S. Application Data

(63) Continuation of application No. 12/806,945, filed on Aug. 24, 2010, now Pat. No. 8,497,063, which is a continuation of application No. 10/523,268, filed as application No. PCT/US03/24460 on Aug. 1, 2003, now Pat. No. 8,211,629.

(60) Provisional application No. 60/400,971, filed on Aug. 1, 2002.

(51) Int. Cl.
*A01N 1/02* (2006.01)
*G01N 33/00* (2006.01)
*A61B 17/43* (2006.01)
*A61D 7/00* (2006.01)

(52) U.S. Cl.
USPC ............ 435/2; 442/73; 600/33; 600/35

(58) Field of Classification Search
CPC ............... C12N 5/061; C12N 5/0612
USPC ............... 435/2; 442/73; 600/33, 35
See application file for complete search history.

(56) References Cited

U.S. PATENT DOCUMENTS

| | | | |
|---|---|---|---|
| 7,094,527 | B2 | 8/2006 | Seidel et al. |
| 8,211,629 | B2 | 7/2012 | Schenk et al. |
| 2004/0210955 | A1 | 10/2004 | Akutsu et al. |
| 2006/0015950 | A1 | 1/2006 | Overstrom et al. |
| 2010/0122359 | A1 | 5/2010 | Suh et al. |
| 2011/0078803 | A1 | 3/2011 | Schenk et al. |

OTHER PUBLICATIONS

Canadian Patent Application No. 2,532,376; OA mailed Jul. 17, 2013, total 3 pages.
U.S. Appl. No. 60/400,971, filed Aug. 1, 2002.
Patent Cooperation Treaty Patent Application No. PCT/US2003/024460, filed Aug. 1, 2003.
Altermatt, et al. Effects of Age and FSH on Collection of Equine Oocytes and Developmental Competency After Intracytoplasmic Sperm Injection. Theriogenology,2007;68,pp. 513-514.
Altermatt, et al. Effects of Age and Equine Follicle-Stimulation Hormone (eFSH) on Collection and Viability of Equine Oocytes Assessed By Morphology and Developmental Competency After Intracytoplasmic Sperm Injection (ICSI). Reproduction, Fertility and Development, 2009; 21, pp. 615-623.
Altermatt, et al. Effect of Mare Age on Oocyte Morphology and Developmental Competence after ICSI. Reproduction, Fertility and Development, 2008; 20(1), pp. 215-216.
Campos-Chillon, et al. Vitrification in Vivo of Large Equine Embryos after Vitrification or Culture. Reproduction, Fertility and Development, 2006; 18(2), p. 151.
Campos-Chillon, et al. Vitrification of Early-Stage Bovine and Equine Embryos. Theriogenology, 2009; 71, pp. 349-354.
Carnevale, et al. Age-Associated Subfertility Before Entry on Embryos into the Uterus in Mares. Equine Vet. J., 1993; Suppl. 15, pp. 31-35.
Carnevale, et al. Assisted Reproductive Techniques. In: Equine Internal Medicine, 3rd Ed. Reed, S.M., et al. WB Saunders, St Louis, 2010; pp. 1083-1087.
Carnevale, Clinical Considerations Regarding Assisted Reproductive Procedures in Horses. Journal of Equine Veterinary Science, 2008; vol. 28, No. 11, pp. 686-690.
Carnevale, et al. Clinical Use of Intracytoplasmic Sperm Injection in Horses. AAEP proceedings, 2007; 53, p. 560.
Carnevale, et al. Collection, Evaluation and Use of Oocytes in Equine Assisted Reproduction. Vet Clin Equine, 2006; 22, pp. 843-856.
Carnevale, et al. Comparison of Culture and Insemination Techniques for Enquine Oocyte Transfer. Theriogenology, 2000; 54, pp. 981-987.
Carnevale, et al. Defective Oocytes as a Cause of Subfertility in Old Mares. Biol Reprod Mono 1 (Equine Reproduction VI), 1995; pp. 209-214.
Carnevale, et al. Factors Affecting the Success of Oocyte Transfer in a Clinical Program for Subfertile Mares. Theriogenology, 2005; 64, pp. 519-527.
Carnevale, et al. Foals Produced after ICSI Using Frozen, Sex-Sorted, Refrozen Sperm, Reproduction, Fertility and Development, 2009; 21(1), p. 228.
Carnevale, et al. Use of Oocyte Transfer in a Commercial Breeding Program for Mares with Reproductive Abnormalities. JAVMA, 2001; vol. 218, No. 1, pp. 87-91.
Couthinho Da Silva, et al. Effect of Time of Oocyte Collection and Site of Insemination on Oocyte Transfer in Mares. Journal of Animal Science, 2002; 80, pp. 1275-1279.
Heindryckx et al. Embryo Development After Successful Somatic Cell Nuclear Transfer to in Vitro Matured Human Germinal Vesicle Oocytes. Human Reprod., May 17, 2007, pp. 1-9.
Couthinho Da Silva, et al. Oocyte Transfer in Mares with Intrauterine of Intraoviductal Insemination Using Fresh, Cooled, and Frozen Stallion Semen. Theriogenology, 2004; 61, pp. 705-713.
MacLellan, et al. Vitrification, warming, ICSI and Transfer of in Vivo Matured Equine Oocytes. 10th International Symposium on Equine Reproduction; Lexington, KY (Supplement of Anim Reprod Sci, 2010; 121S, pp. S260-S261).
McKinnon, et al. Heterogenous and Xenogenous Fertilization of in Vivo Matured Equine Oocytes. Equine Nutrition & Physiology Society, 1988: 8(2), pp. 143-147.
Scott, et al. Embryo Development Rates after Transfer of Oocytes Matured in Vivo, in Vitro, or within Oviducts of Mares. Theriogenology, 2001; 55, pp. 705-715.
Squires, et al. Use of Sexed, Refrozen Spermatozoa for ICSI. Havemeyer Foundation 7th International Sym Equine Embryo Transfer, 2008; pp. 54.
Stokes, et al. Effect of Developmental Stage of ICSI-Produced Equine Embryos on Pregnancy Rates. Reproduction, Fertility and Development, 2008; 21(1), p. 164.

*Primary Examiner* — Marcia S Noble
(74) *Attorney, Agent, or Firm* — Craig R. Miles; CR Miles, P.C.

(57) ABSTRACT

A sperm cell process system providing to generate sperm cell insemination samples having controlled sperm cell fertility characteristics of sperm cells.

14 Claims, 2 Drawing Sheets

SPERM CELL SEPARATION SYSTEM

This United States Patent Application is a continuation of U.S. patent application Ser. No. 12/806,945, filed Aug. 24, 2010, which is a continuation of U.S. patent application Ser. No. 10/523,268, filed Jul. 7, 2005, which is the National Stage of International Patent Cooperation Treaty Patent Application No. PCT/US2003/024460, filed Aug. 1, 2003, which claims the benefit of United States Provisional Patent Application No. 60/400,971, filed Aug. 1, 2002, each hereby incorporated by reference herein.

I. TECHNICAL FIELD

Sperm cell insemination samples having selectably controlled sperm cell fertility characteristics produced through entrainment in a fluid stream having correspondingly selectably adjustable flow characteristics and methods of assessing comparative of sperm cell insemination sample fertility.

II. BACKGROUND

Pre-selection of sex has been accomplished in many species of livestock following the development of safe and reliable methods of separating sperm cells into enriched X chromosome bearing and Y chromosome bearing populations. See for example methods and apparatus disclosed by WO 00/06193; WO 02/043574; WO 01/85913; WO 99/33956; WO 01/40765; WO 98/34094; WO 99/42810; WO 02/043486.

A significant problem with sex selected sperm cells may be that separation of sperm cells at rates sufficient to produce sex selected insemination samples or sex selected inseminates which are viable or sufficiently fertile for commercial application by conventional technology has necessitated increasing fluid stream pressure of flow cytometers or flow sort instruments to about 50 pounds per square inch. With respect to sperm cells of many species of mammals entrained in fluid streams having flow characteristics resulting from this application of pressure the viability, motility, or other fertility characteristics altered.

Another significant problem with sex selected sperm cell inseminates or sex selected sperm cell insemination samples can be the vast difference in sperm cell fertility characteristics which can vary greatly between samples. As such, success of artificial insemination performed under substantially identical conditions can result in correspondingly different pregnancy rates.

Another significant problem with existing sperm cell sex selection technology can be the lack of an assay from which fertility of sex selected sperm cells can be compared directly in-vivo (for example, in conjunction with artificial insemination procedures) and in-vitro (for example, in conjunction with IVF procedures).

The instant invention addresses the variety of problems associated with reduced sperm cell fertility spermatozoa that have been separated into enriched X-chromosome bearing and Y-chromosome bearing populations and the lack of heterospermatic assays to compare function and fertility of separated or sorted sperm cells, and in particular flow sorted sperm cells.

III. DISCLOSURE OF THE INVENTION

Accordingly, the broad object of the invention provides devices and methods of using such devices to control sperm cell fertility characteristics of sperm cells isolated from semen obtained from a male of species of mammal, such as motility, viability, fertilization rate, cleavage rate, blastocyst rate, or the like.

Providing controlled sperm cell fertility in accordance with the invention can be achieved with the sperm cells obtained from numerous and varied species of mammals, including without limitation, mammals selected from the group consisting of a bovine species of mammal, an equine species of mammal, an ovine species of mammal, a canine species of mammal, a feline species of mammal, a swine species of mammal, a marine species of mammal, a deer species of mammal, a primate species of mammal, a goat species of mammal, or a species of mammal listed by Wilson, D. E. and Reeder, D. M., Mammal Species of the World, Smithsonian Institution Press, (1993), hereby incorporated by reference herein.

With respect to certain embodiments of the invention, controlled sperm cell fertility characteristics comprises affirmative selection of fertility characteristics in advance of isolating sperm cells from the semen of the male of the species of mammal and application of the invention to alter sperm cell fertility characteristics to provide the fertility characteristics desired. With respect to other embodiments of the invention, sperm cell treatment conditions are selected within a broader range of sperm cell treatment conditions that can be used treat sperm cells of a particular species of mammal to obtain sperm cells having controlled fertility characteristics. Controlled fertility characteristics can comprise a desired proportion of motile sperm cells, intact acrosomes, viable sperm cells within a population of treated sperm cells; or can comprise a desired cleavage rate of oocytes or rate of blastocyst formation when treated sperm cells are utilized to fertilize oocytes in vitro; or can comprise a desired pregnancy rate or sex ratio of offspring when treated sperm cells are utilized for artificial insemination. With respect to certain embodiments of the invention, a greater proportion of motile sperm cells, a greater proportion of viable sperm cells, a greater proportion of intact acrosomes, or a greater number of fertile sperm cells within a treated sperm cell population can be achieved compared to conventional treatment of the same of sperm cell population. Certain embodiments of the invention allow provision of sperm cells having controlled fertility characteristics which are not substantially different than, or are substantially comparable to, the fertility characteristics of sperm cells in fresh ejaculated semen. In other instances, application of certain embodiments of the invention can if desired result in sperm cells having controlled fertility characteristics which are substantially different than those of sperm cells of fresh ejaculated semen. In particular, certain embodiments of the invention can be used to provide bovine sperm cells having controlled fertility characteristics or can be used to provide equine sperm cells having controlled fertility characteristics, which if desired can be provided with fertility characteristics substantially comparable to the fertility characteristics of bovine sperm cells or equine sperm cells within freshly ejaculated bovine or equine semen.

Another broad object of the invention can be to provide sperm cell insemination samples having controlled sperm cell fertility characteristics, such sperm cell insemination samples, without limitation, can be configured for artificial insemination of a female of a species of mammal, in vitro fertilization of oocytes, or intracytoplasmic injection of sperm cells, or the like.

Another broad object of the invention can be to provide methods of sex selecting sperm cells that can provide affirmative control of sperm cell fertility characteristics such as motility, viability, fertilization rate, cleavage rate, blastocyst rate, or the like. One aspect of this broad object of the invention can be to provide flow cytometry or cell sorting devices or methods of flow cytometry or cell sorting which allows affirmative control of the fertility characteristics of sex selected sperm cells.

Another object of the invention can be to provide sex selected bovine sperm cell insemination samples having controlled sperm cell fertility characteristics configured for artificial insemination of a female of a bovine species of mammal containing between about 100,000 and about 3,000,000 sex selected bovine sperm cells having controlled sperm cell fertility characteristics.

Another object of the invention can be to provide sex selected equine sperm cell insemination samples having controlled sperm cell fertility characteristics configured for artificial insemination of a female of an equine species of mammal containing between about 5,000,000 and about 50,000,000 sex selected bovine sperm cells having controlled sperm cell fertility characteristics.

Another significant object of the invention can be to provide devices or methods of maintaining controlled sperm cell fertility characteristics of sperm cells with respect to processing of sperm cells, storage of sperm cells, or use of sperm cells, including, but not limited to, insemination of female mammal(s) or fertilization of oocyte(s).

Another significant object of the invention can be to provide methods of artificially inseminating females of a species of mammal with sperm cell insemination samples having controlled sperm cell fertility characteristics. With respect to certain embodiments of the invention, methods of insemination with a low or reduced number of sperm cells having controlled fertility characteristics compared to the usual number or typical number of sperm cells used in such artificial insemination procedures whether or not such sperm cells are separated into enriched X chromosome bearing or Y chromosome bearing sperm cell populations.

Another broad object of the invention can be to provide a method of assessing comparative fertility of sperm cell populations. Certain embodiments of the invention provide a method of assessing comparative fertility of sperm cells from different males of a species of mammal when sperm cells from each male are exposed to substantially the same flow cytometric treatment. Other embodiments of the invention provide a method of assessing comparative fertility of sperm cells from the same male of a species of mammal which are exposed to different flow cytometric treatments. Certain embodiments of the invention provide methods of showing comparative fertility of sperm cells having controlled fertility characteristics.

Naturally, further significant objects of the invention are made clear in the proceeding description of the invention.

IV. BRIEF DESCRIPTION OF DRAWINGS

V. MODE(S) FOR CARRYING OUT THE INVENTION

A semen or sperm cell process system to maintain, enhance, assay, test, or determine the biological, chemical, physical, physiological, or functional attributes of sperm cells within the context of various collecting, handling, storage, transportation, separation, or insemination procedures.

An embodiment of the invention can comprise obtaining a sperm cells from a species of mammal as broadly defined above. The sperm cells can then be entrained in a fluid stream having flow characteristics. The fluid stream within a conduit has flow characteristics influenced by the rheological properties of the fluid stream, the configuration or geometries of the conduit in which the fluid stream flows, as well as external forces applied to the fluid stream such as hydrostatic pressure, oscillatory vibrations, piezoelectric vibrations, oscillations in heat, or the like.

Importantly, these flow characteristics of the fluid stream contribute to the amount of pressure required to move fluid within the conduit As a non-limiting example, in flow cytometry fluid moves within a relatively large cross sectional area and then within a relatively small cross sectional area past an analysis interface to a final collection point.

This type of configuration or geometry along with rheologic properties of the fluid stream can create localized forces such as compressive forces, sheer forces, or the like, which can have influence the physical integrity of particles such as sperm cells entrained in the fluid stream.

Figure 1:
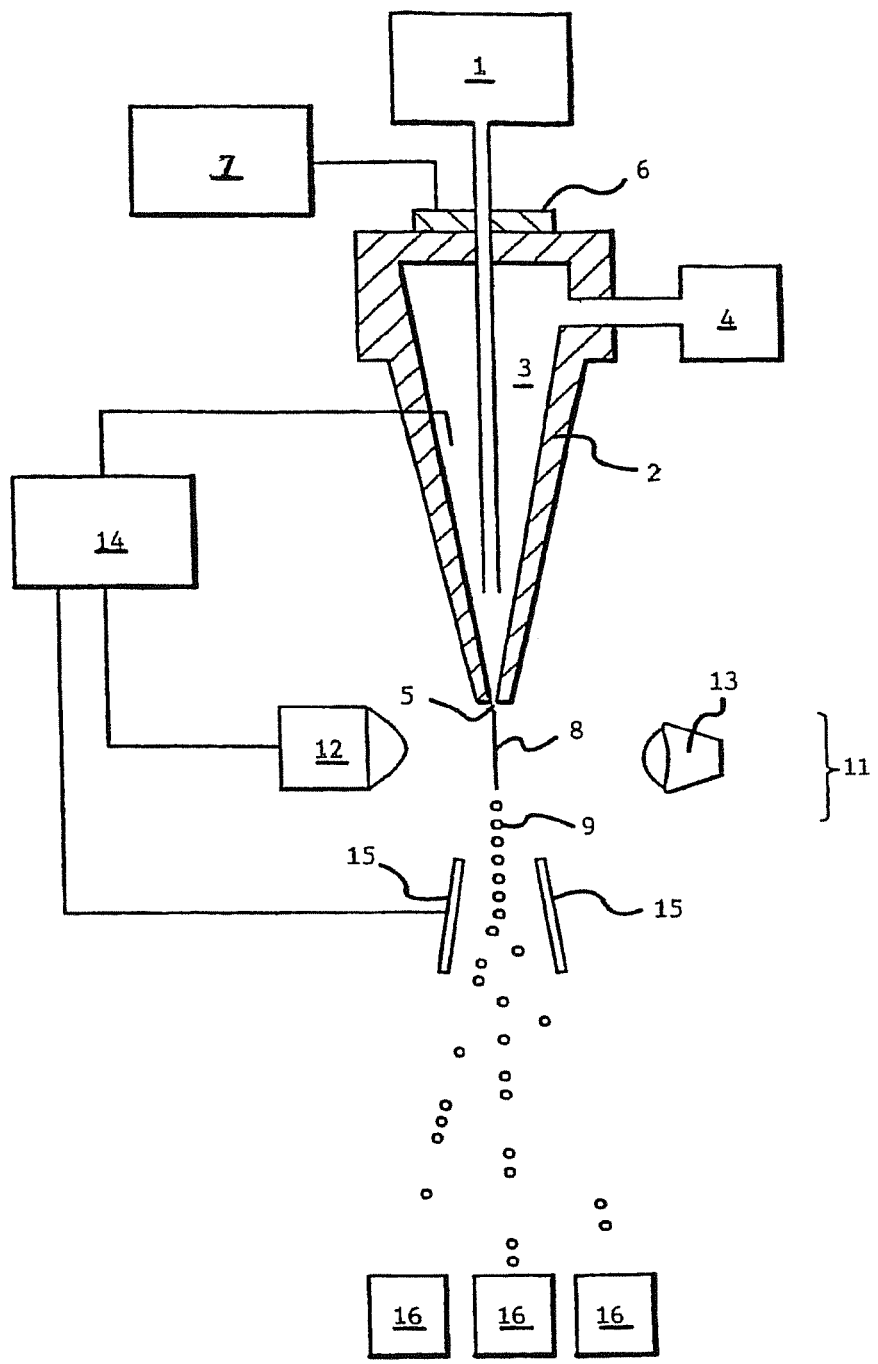
FIG. 1 is a schematic diagram of a sorter system according to a flow cytometer separation technique for the present invention.

With respect to those embodiment of the invention which include components of or steps involving flow cytometry or cell sorting as a means to analyze, separate based upon a sperm cell characteristic, sex select, or other wise process sperm cells, a conceptual non-limiting flow cytometer or cell sort instrument is shown by FIG. 1.

A flow cytometer or cell sort instrument includes all or a portion of the components shown by FIG. 1 including with out limitation, a sperm cell source (1) which acts to establish or supply sperm cells to analyze, separate, control fertility characteristics, or be otherwise treated.

Sperm cells are deposited within a nozzle (2) in a manner such that sperm cells are surrounded by a sheath fluid (3). Any sheath fluid compatible with the flow cytometer or flow sort instrument and which provides an acceptable environment for sperm cells during flow analysis or processing can be utilized with the invention, including without limitation, sheath fluids which contain, individually or in various combinations, a phosphate buffered saline, a citrate solution (such as a 2.9% sodium citrate solution), or a HEPES buffered solution.

The sheath fluid (3) is usually supplied by some sheath fluid source (4) so that as the sperm cell source (1) supplies sperm cells, the sheath fluid (3) is concurrently fed through the nozzle (2). In this manner, the sheath fluid (3) forms a sheath fluid environment for the cells. Since the various fluids are provided to the flow cytometer at some pressure, they flow out of nozzle (2) and at the nozzle orifice (5).

By providing some type of oscillator (6) which may be very precisely controlled through an oscillator control (7), pressure waves may be established within the nozzle (2) and transmitted to the sheath fluid exiting the nozzle (2) at nozzle orifice (5). Since the oscillator (6) thus acts upon the sheath fluid (3), the stream (8) exiting the nozzle orifice (5) eventually and regularly forms drops (9). Because the cells are surrounded by a sheath fluid environment, the drops (9) may contain within them individually isolated sperm cells (10).

Since the droplets (9) generally contain isolated sperm cells (10), the flow cytometer or cell sorter instrument can distinguish between and separate droplets based upon a distinguishing sperm cell characteristic(s) of the sperm cell contained within a droplet (9). This is accomplished through a sperm cell sensing system (11). The sperm cell sensing system involves at least some type of detector (12) which responds to sperm cells contained within each droplet (9).

One type of sperm cell sensing system (11) is as discussed at length in U.S. Pat. No. 5,135,759 to Johnson, hereby incorporated by reference herein. As the Johnson patent explains for sperm cells, the cell sensing system (11) may cause an action depending upon the relative presence or relative absence of a particular dye which may be excited by some stimulant such as the beam of a laser (13). While each type of sperm cell can be stained with a dye, the differing length of the X-chromosome and the Y-chromosome causes different levels of staining. Thus, by sensing the degree of dye present in each sperm cells it is possible to discriminate between X-chromosome bearing sperm and Y-chromosome bearing sperm by their differing emission levels. Alternate optics, detection and sperm cell analysis systems are known which can also be used in accordance with the invention and it is intended that the description provided by the Johnson patent is for illustrative purposes so that the numerous and varied uses of the invention can be understood. See also, WO 01/85913, hereby incorporated by reference herein.

In order to achieve the ultimate separation and isolation of the appropriate cells in a flow cytometer or cell sort instrument separation technique, the signals received by sensor (12) are fed to some type of sorter discrimination system (14) which very rapidly makes the decision and can differentially charge each droplet (9) based upon whether the desired cell does or does not exist within that droplet (9). In this manner the sorter discrimination system (14) acts to permit the electrostatic deflection plates (15) to deflect droplets (9) based on whether or not they contain the a sperm cell having certain sperm cell characteristics. As a result, the flow cytometer or cell sorter instrument acts to separate the cells by causing them to land in one or more collection containers (16). Thus by sensing some property of the sperm cells the flow cytometer or cell sorter instrument can discriminate between cells based on a particular characteristic and place them in the appropriate collection container (16). In certain flow cytometers or cell sorter instruments, the X-bearing sperm droplets are charged positively and thus deflect in one direction, the Y-bearing sperm droplets are charged negatively and thus deflect the other way, and the wasted stream (that is unsortable cells) is uncharged and thus is collected in an undeflected stream into a suction tube or the like.

Figure 2:
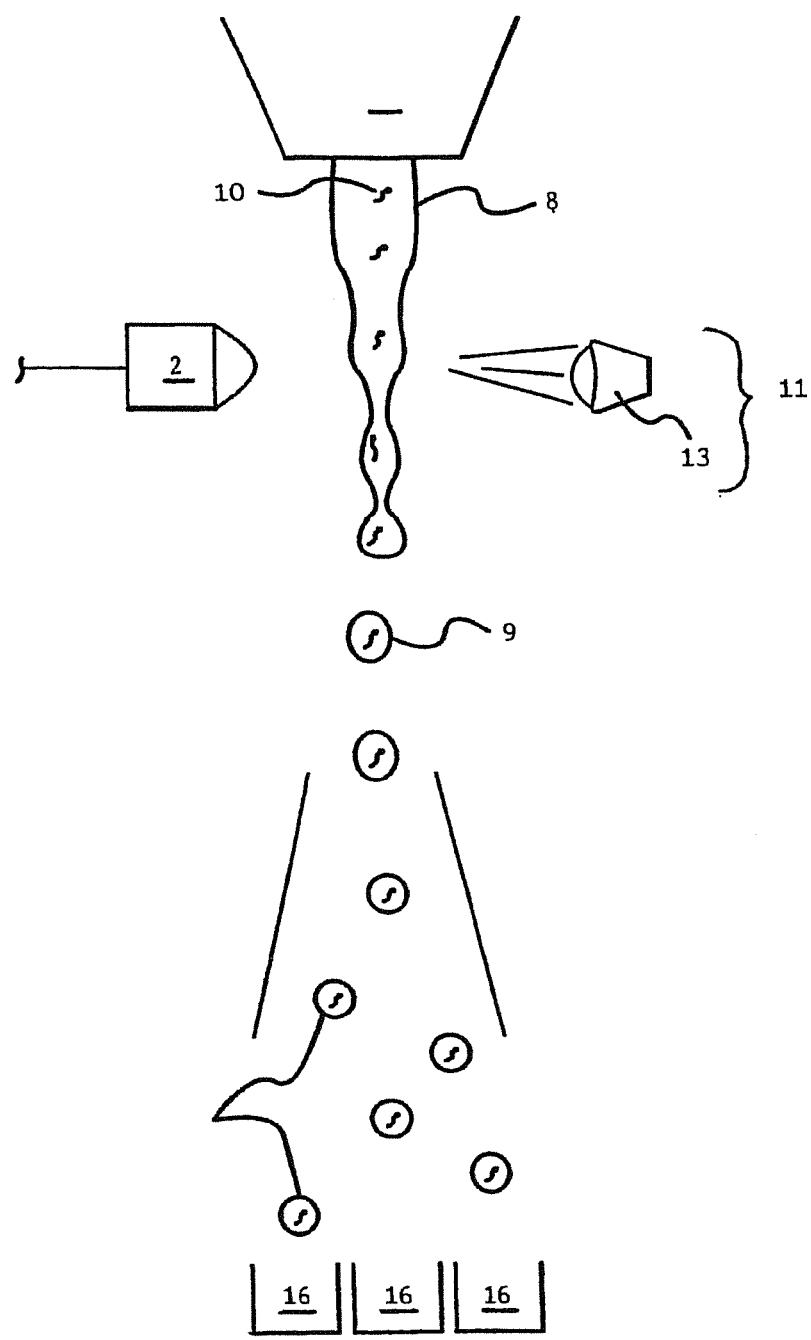
FIG. 2 is a diagram of the entrained cells in the free fall area of a typical flow cytometer.

Now referring primarily to FIG. 2, the process can be even further understood. As shown in that figure, the nozzle (2) emits a stream (8) which because of the oscillator (7) (not shown in FIG. 2) forms drops (9). Since the cell source (1) (not shown in FIG. 2) may supply sperm cells (10) which as described by Johnson can be stained (or in certain embodiments of the invention unstained as when using DIC technology), the light emission generated by the beam generated by laser (or illumination source when using DIC technology) (13) incident upon the dye (the sperm head when DIC technology is utilized) is differentially determined by sensor (12) so that the existence or nonexistence of a charge on each drop (9) as it separates from stream (8) can be controlled by the flow cytometer. This control results in positively charged, negatively charged, and uncharged drops (9) based upon their content. As shown in FIG. 2, certain drops are shown as deflected drops (17). These deflected drops (17) are those containing sperm cells (10) which can be one or the other sex. They are then deposited in the appropriate collector (16) thereby generating a population of sex selected sperm cells.

Whether the fluid stream occurs within the context of a flow cytometer, cell sorter, or other device which entrains sperm cells within a fluid stream, the flow characteristics of the stream can be characterized and adjustment means for altering flow characteristics of the fluid stream can be introduced to increase or decrease forces such as compressive forces, sheer forces, or the like, such that particles entrained in the fluid stream can be physically, physiologically, functionally, or mechanically altered.

As such a selectably adjustable range of fluid stream characteristics for a flow path can be generated using the adjustment means and can be expressed as an incremental measure. For example, alteration of fluid stream characteristics within a flow cytometer or cell sort instrument context can be incrementally adjusted and measured in pounds per square inch and typically allow the incremental increase or decrease in fluid stream pressure between about 20 pounds per square inch and 100 pounds per square inch with a commensurate increase or decrease in fluid stream or sheath fluid velocity.

In accordance with certain embodiments of the invention, sperm cells of a particular species of mammal are entrained in a fluid stream having adjustable fluid stream flow characteristics. Fluid stream flow characteristics are then selectably adjusted over an incrementally measured range in which the entrained sperm cells remain viable. Sperm cell fertility characteristics are then assessed for each of a plurality of sperm cell samples taken in correspondence to each of a plurality of flow characteristics generated within the measured range.

Subsequently, sperm cell fertility characteristics with respect to sperm cells from a species of mammal or individual members of a species of mammal can be controlled and sperm cell insemination samples can be generated having the desired sperm cell fertility characteristics.

For example, sperm cells from each of six bulls were stained with 125.mu.m Hoechst 33342 for 45 min at 34 .degree. C., and bulk-sorted (passed through a flow cytometer or cell sorter instrument without sorting into subpopulations) or sorted with a flow cytometer having a nozzle with an internal diameter of 70.mu.m into X-chromosome bearing or Y-chromosome bearing (or both) populations at about 95% accuracy with the fluid stream having a pressure of at 30 pound per square inch, 40 psi, or 50 psi. Lowering the fluid stream pressure from 50 psi to 30 psi reduced sorting rate by only 2 to 3%.

The sperm cells were subsequently cooled to 5.degree. C. and concentrated by centrifugation, loaded into 0.25 ml straws with about 2.times.10.sup.6 total sperm cells per 100.mu.l column, and frozen using a vapor freezing method along with unsorted controls. The sperm cells in the straws were subsequently thawed.

Sperm cells were then evaluated with respect to various sperm cell fertility characteristics blindly by two observers at 30 and 120 min post-thaw for progressive motility, as well as by flow cytometry 105 min post-thaw, for percent live sperm cells by PI stain, and by CASA analysis 120 min post-thaw using the Hamilton Thorne system. The entire procedure was twice replicated.

Factorial ANOVA indicated that both bull and pressure effects were significant (P<0.005, Table I). TABLE-US-00001 TABLE 1 Responses of sperm post-thaw to different system pressures during sorting.sup.a Pressure (psi) Response 50 40 30 Unsorted Control 30 min motility (%) 44.7 48.6 49.6 52.1 120 min motility (%) 34.5 40.8 42.7 40.8 Live sperm (%) 51.7 55.7 57.8 58.5 CASA total motility (%) 25.1 37.2 40.9 34.8 CASA ALH* 6.0 7.6 7.8 8.8.sup.aAll statistically significant, P<0.005.*Amplitude of lateral head displacement.

Higher numbers mean less stiff and more normal motility. There were typical differences among bulls in all responses. However, the bull by treatment interactions were small with one exception, meaning findings apply similarly to most bulls in the population. The flow characteristics of the fluid stream adjusted incrementally to increase pressure affected substantially all sperm cell fertility characteristics measured, however, only highly statistically significant ones are in Table 1.

As can be understood, there was significant change in sperm cell fertility characteristics between sperm cell samples taken at about 50 psi and at about 40 psi, and then a much smaller change between about 40 psi and about 30 psi, indicating that the effect on sperm cell fertility characteristics can not be assumed linear. For bovine sperm cells exposed to the flow characteristics described at 30 psi, sperm cell fertility characteristics were substantially the same as nonsorted controls or comparable to nonsorted controls, and for a few responses better, if sperm cells are to be used for insemination or artificial insemination of females of the bovine species. Similar procedures were conducted with sperm cells obtained from stallions with similar results and conclusions.

Sperm cell fertility characteristics can be controlled and with respect to sperm cells obtained from mammals. For most species of mammals altering fluid stream characteristics to incrementally reduce fluid stream pressure, whether in the context of flow cytometry or otherwise, can result in a graded series of corresponding sperm cell samples having altered sperm cell fertility characteristics which may be used for a variety of procedures including artificial insemination, in vitro fertilization, or intracytoplasmic injection as described below.

The invention provides a alternate tests to assess binomial responses such as pregnant/not pregnant, which typically require large numbers of animals per treatment to obtain statistical significance unless treatment differences are fairly large. One embodiment of the invention which can amplify differences in sperm cell fertility characteristics of sex selected sperm due to treatment differences comprises competitive, or heterospermic, fertilization, mixing sperm of different treatments or males before insemination, and determining the proportion of embryos, fetuses or offspring derived from each male or treatment For example, fertility after sex selection of sperm cells by flow cytometry or by cell sorting for DNA content at two different fluid stream pressures can be assessed using heterospermic insemination using sex as the genetic marker. Sperm cells from each of two bulls was sorted into X-chromosome bearing or Y-chromosome populations, or both, at about 95% accuracy with the fluid stream pressure adjusted to either 30 psi or 50 psi. After concentrating sperm cells post-sort by centrifugation, $1 \times 10^6$ X-chromosome bearing sperm cells sorted at 30 psi were placed in 0.25-mL straws with $1 \times 10^6$ Y chromosome bearing sperm cells sorted at 50 psi for each bull, as well as the converse in other straws: $1 \times 10^6$ Y-sperm at 30 psi plus $1 \times 10^6$ X-sperm at 50 psi. These sperm cells, along with unsorted controls, were then frozen, thawed some months later, and inseminated into the body of the uterus of 85 Holstein heifers either 12 or 24 h after observed estrus with subgroups balanced across two inseminators.

Two months post-insemination, 81% of the 43 heifers becoming pregnant had fetuses of the sex (determined by ultrasound) corresponding to the sex of sperm processed at 30 psi. This differed from the 50:50 sex ratio expected (P<0.01), if there was no difference in sperm cell fertility characteristics of sperm cells sorted at the two pressures. The pregnancy rate with sex selected sperm at $2 \times 10^6$ sperm per dose was 51% (43/85); this was similar to the controls of $20 \times 10^6$ unsexed sperm per dose from the same ejaculates, 39% (9/23).

Another embodiment of the invention provides a method altering the cleavage rate and rate of blastocyst formation using sperm cells having controlled sperm cell fertility characteristics. Two bovine sperm cell samples each having controlled fertility characteristics were generated by flow sorting bovine sperm cells at 40 psi and 50 psi respectively. Dose response of sperm cell concentration in the fertilization medium was conducted with X-chromosome bearing sperm cells and Y-chromosome bearing sperm cells from each sperm cell sample. Thus, a multifactorial procedure comprising 2 fluid stream pressures, 3 sperm cell concentrations (1, 0.33 and $0.11 \times 10^6$ sperm/ml), 6 bulls and 2 sexes can be conducted.

About 2,000 oocytes were aspirated from about 2 mm to about 8 mm follicles from slaughterhouse ovaries. Chemically defined media (CDM) were used throughout as described by Journal of Animal Sciences, 78:152-157 (2000), hereby incorporated by reference herein. Maturation took place in M-CDM supplemented with 0.5% FAF-BSA, 15 ng/ml NIDDK-oFSH-20, 1 $\mu$g/ml USDA-LH-B-5, 0.1 $\mu$g/ml $E_2$, 50 ng/ml EGF and 0.1 mM cysteamine for 23 h at 38.8°C. and 5% $CO_2$ in air. Sorted sperm cells frozen with $2 \times 10^6$ cells per straw were thawed and centrifuged at 400 g through 2 ml 45% and 2 ml 90% Percoll gradients for 20 min. Then the supernatant was discarded and 2 ml of FCDM supplemented with 0.5% FAF-BSA, 2 mM caffeine and 0.02% heparin was added to the sperm pellet and centrifuged at 500 g for 5 min. The supernatant was discarded leaving approximately 50 $\mu$l of sperm suspension. Matured oocytes were washed once in FCDM and transferred in groups of 15 in 5 $\mu$l into 25-$\mu$l drops of FCDM under mineral oil. Fertilization took place by adding 10 $\mu$l of sperm suspension per drop for 18 h at 38.8°C., 5% $CO_2$ in air. Presumptive zygotes were cultured in CDM1 for 2 d and CDM2 for 4.5 d at 38.5°C., 5% $O_2$, 5% $CO_2$ and 90% $N_2$. On day 7.5, blastocyst development was evaluated: Quality 1 to 4 (1 being excellent and 4 being poor) and stage of development, 6 to 8 (6 full, 6.5 expanding, 7 expanded, 7.5 hatching and 8 hatched blastocysts). Data (Table 1) were analyzed by ANOVA and first deviation after arc sin transformation.

Cleavage (53.6 and 43.6%) and blastocyst (18.2 and 14.7%) rates were higher for procedures utilizing sperm cells having controlled sperm cell characteristics obtained at about 40 psi than at about 50 psi (P<0.01). There was no interaction between dose and pressure; therefore, there was a similar advantage to lower pressure at each sperm concentration. A clear dose response of sperm cell concentration for cleavage and blastocyst production was found (Table 2). Also, there were large differences among bulls (P<0.01) for both responses, and there was a bull.times.dose interaction (P<0.01) for % cleaved. The data indicate that the sperm dose should be >$1.0 \times 10^6$/ml for some bulls. Embryo quality was higher (P<0.01) for Y-sperm than X-sperm (1.12 vs 1.57). Others have noted this for IVF embryos when embryos were sexed, and this effect now is confirmed with sexed sperm.

TABLE 2 Cleavage (%, C) and blastocysts (%, B) per oocyte data presented by bull.

| Sperm conc. ($10^6$) | Bull H023 | | H024 | | H025 | | H026 | | H027 | | H028 | | Avg | |
|---|---|---|---|---|---|---|---|---|---|---|---|---|---|---|
| | C | B | C | B | C | B | C | B | C | B | C | B | C | B |
| 0.11 | 18 | 1 | 6 | 1 | 4 | 11 | 36 | 15 | 20 | 7 | 54 | 15 | 30$^a$ | 8$^a$ |
| 0.33 | 44 | 4 | 7 | 2 | 72 | 31 | 62 | 21 | 29 | 11 | 68 | 18 | 47$^b$ | 14$^b$ |
| 1.0 | 56 | 18 | 35 | 14 | 85 | 43 | 83 | 34 | 72 | 27 | 85 | 29 | 69$^c$ | 28$^c$ |

$^{a,b,c}$Values without common superscripts within groups differ, P<0.01.

**Fertility of sorted sperm has been low compared to unsorted control sperm, due partly to mechanical damage during sperm sorting by flow cytometry. Lowering system pressure improved both sperm quality and fertility in IVF.

The present study evaluated the effect of system pressure during sperm sorting and extended maturation of oocytes on development of embryos after ICSI. Sperm from each of 3 bulls were stained with 125 .mu.M Hoechst 33342 for 45 min at 34.degree. C., sorted into X- and Y-chromosome bearing populations at 95% accuracy with the pressure of SX MoFlo® sorters at 40 or 50 psi, and then cryopreserved. Fifty bovine oocytes obtained from slaughterhouse ovaries were placed per well with 1 ml of CDM1 supplemented with 0.5% FAF-BSA, 2 mM glucose, 50 ng/ml EGF, 15 ng/ml NIDDK-oFSH-20, 1.mu.g/ml USDA-LH-B-5, 1 .mu.g/ml E2 and 0.1 mM cysteamine, and then matured for 24 h or 30 h at 38.5.degree. C., 5% CO.sub.2 in air. Cumulus cells of matured oocytes were removed by vortexing, and oocytes with a polar body were selected. Motile sperm from sorted frozen-thawed semen were recovered by centrifugation through 2 ml each of 45 and 90% Percoll, and the concentration adjusted to 4.times.10.sup.6/ml. Matured oocytes were divided into two injection groups, ICSI and sham injection using a Piezo injection system. The outer diameter of the sperm injection pipette was 8-10.mu.m. All manipulations were performed at room temperature (24-25.degree. C.). After injection, oocytes were activated with 5.mu.M ionomycin for 4 min, cultured in 50.mu.l of CDM1 at 38.5.degree. C. under 5% CO.sub.2, 5% O.sub.2 and 90% N.sub.2, and assessed for cleavage at 72 h post-injection. Uncleaved oocytes from ICSI and sham injected groups were stained with orcein and evaluated for fertilization status. Cleaved embryos were further cultured and blastocyst development was evaluated on day 7.5 after injection. Data were subjected to ANOVA; the arc sin transformation was used for percentage data.

With 24 h matured oocytes, there were no differences (P>0.1) between sperm sorted at 40 versus 50 psi for cleavage or blastocyst rates, nor was there pressure.times.bull interaction. There were significant effects of bulls for all responses studied (P<0.05). When injected with sperm sorted at 40 psi, oocytes matured for 30 h resulted in a higher cleavage rate than 24 h matured oocytes (22.9 versus 12.2%, P<0.05), with no difference P>0.1) in blastocyst rate. Overall blastocyst development was higher in ICSI than in sham injection (7.5 versus 1.3%, P<0.05). When uncleaved oocytes from 24 h maturation were evaluated for fertilization status, ICSI showed higher percentage with 2 polar bodies and/or decondensed sperm compared to sham injection (15.7 versus 1.7%, P<0.05). With 30 h matured oocytes there was no difference in fertilization status between those two groups. We conclude that there was no difference in cleavage or development to blastocysts after ICSI using motile sperm that had been sorted at 40 vs 50 psi.

In another embodiment of the invention, heterospermic insemination using sex as the genetic marker can be used to rank fertility of males and to rank fertility of sperm treatments not involving sperm sexing. Current in vitro tests of sperm function are not highly correlated with male fertility, and homospermic inseminations require hundreds of inseminations per treatment to obtain accurate fertility data. Heterospermic insemination, mixing the sperm of two or more males, provides an accurate estimation of relative fertility in most species examined.

Frozen, flow-sorted sperm from 4 groups of 4 bulls were thawed and inseminated into heifers 12 h or 24 h following onset of estrus in all combinations of 3 bulls within groups (ABC, ABD, ACD, BCD). Equal numbers of progressively motile sperm were inseminated from each bull, totaling 600,000 motile sperm post-thaw. Half of each inseminate was deposited into each uterine horn. Embryos were collected nonsurgically 14.5 to 20 days following estrus. Collections yielded 165 elongating embryos from 332 heifers (48%). Polymorphic DNA markers were used to genotype embryos to determine the sire of each embryo biopsy. After genyotyping, 118 of the 165 embryos could be assigned a specific sire. Heterospermic indices for ranking each bull group were calculated using the maximum likelihood analysis theorem. Each bull within groups was ranked based on these indices (Table 1). In group 1, the fertility of the poorest bull was significantly lower (P<0.05) than two other bulls. In group 2, the dominant bull had the highest index (P<0.05). Similar distinctions could be made in groups 3 and 4. However, in three of the groups the fertility of some bulls was not clearly high or low (P>0.05). TABLE-US-00003 TABLE 1 Heterospermic indices .+-. SE for individual bulls within groups. Group 1 Group 2 Group 3 Group 4 1.47.+-. 0.41.sup.a 2.43.+-. 0.43.sup.a 1.68.+-. 0.44.sup.a 0.92.+-. 0.36.sup.a,b 0.44.+-. 0.27.sup.a,b 0.22.+-. 0.15.sup.b 1.09.+-. 0.39.sup.a,b 0.46.+-. 0.20.sup.a 1.84.+-. 0.46.sup.a 0.90.+-. 0.35.sup.b 0.83.+-. 0.31.sup.a,b 2.02.+-. 0.40.sup.b 0.25.+-. 0.17.sup.b 0.45.+-. 0.23.sup.b 0.40.+-. 0.22.sup.b 0.59.+-. 0.24.sup.a .sup.a,bIndices without common superscripts differ, P<0.05.

With these procedures, an average of 30 genotyped embryos per group of 4 bulls enabled detection of bulls with clearly differing fertility. Sperm treatments also could be evaluated with this technique. This in vivo test requiring few females rapidly provides information concerning which bulls have relatively high or low fertility.

The population of calves obtained by artificial insemination of females with sex selected sperm cells in accordance with the invention are virtually identical to controls using unsex selected sperm cells. Furthermore, artificial insemination of females with sex selected sperm resulted in approximately 90% of calves of the planned sex. As described above, sperm cells can be sex selected on the basis of DNA content by flow cytometry or by cell sorting after staining with H33342. The sex selected sperm cells can then be cryopreserved as described in Theriogenology, 52:1375"Cryopreservation of Flow-Sorted Bovine Spermatozoa", hereby incorporated by reference herein.

Estrus can be synchronized in heifers and cows of various beef and dairy breeds, either by feeding 0.5 mg melengestrol acetate (MGA) daily for 14 d followed by 25 mg prostaglandin F.sub.2 (PGF.sub.2) im 17 to 19 d later or injection of 25 mg PGF.sub.2 im at 12-d intervals. Insemination with either frozen-thawed sex selected insemination samples or frozen-thawed sperm from the same ejaculate have been accomplished at either 12 hours or 24 hours after initial observation of estrus. For each breeding group, about ⅔ of the inseminations were with sexed sperm while control sperm were used in the remainder. Pregnancy and fetal sex were diagnosed by ultrasound 2 months later.

Cattle were managed at 13 farms through calving and weaning under differing levels of management (N=49 to 228 per farm). Data collected included gestation length, birth weight, calving ease (1=normal to 4=Caesarian), weaning weight, neonatal deaths, and deaths from birth to weaning. Not all farms recorded birth and weaning weights. Data were subjected to factorial analysis of variance with factors: management groups, sorted versus control sperm, and sex of calves. The arc sin transformation was used for percentage data. Least-square means are in Table 1. TABLE-US-00004 TABLE 1 Calving results from sexed and control calves Gesta-Neo-tion natal Birth Live at Weaning Treat-length death Calving weight weaning weight ment N (d) (%) ease (kg) (%) (kg) Sexed.sup.a 574 279 3.9 1.31 34.3 92.0 239

Control 385 279 5.9 1.30 34.1 88.9 239.sup.allo significant differences (P>0.1) for any response.

There were no differences (P>0.1) between calves from sexed versus control groups for any response studied, nor were there significant interactions. There were significant effects of management groups for all responses studied (P<0.001 for all except % alive at weaning, P<0.02). Also, there were significant differences (all P<0.001) between female and male calves for birth weight: 32.2 and 35.5 kg; weaning weight: 232 and 246 kg; calving difficulty: 1.20 and 1.42; and gestation length: 278 and 280 d. The sex ratio of the control calves was 51.0% males (N=382). X sort sperm resulted in 87.7% females, while the Y sort sperm produced 93.6% males (N=94). A few calves that were dead at birth did not have sex recorded and are not included. The recent development of flow cytometric separation of stallion spermatozoa has resulted in the production of normal foals with preselected sex. (Lindsey A. C., Morris L. H., Allen W. R., Schenk J. L., Squires E. L., Bruemmer J. E. Equine vet J. 2002, 34: 128-132). For this technology to be accessible, semen will be transported from the flow cytometer to the mare. This study examined the longevity and acrosome status of fresh stallion spermatozoa after sex preselection. Three ejaculates from each of 7 stallions were collected by artificial vagina and shipped to the laboratory at 20.degree. C. for 2-6 h in a skim milk-glucose extender (1:1 v/v). The semen was centrifuged at 400 g for 10 min and the seminal plasma removed. The sperm pellet was resuspended to 100.times.10.sup.6/ml in Kenneys modified Tyrodes medium (KMT), stained with Hoechst 33342 (5 mg/ml, Sigma-Aldrich, St. Louis Mo.), incubated for 30 min and subjected to flow cytometry. The sorted spermatozoa were centrifuged and resuspended to 40.times.10.sup.6 ml in KMT in 250.mu.l aliquots for 48 h storage at either 4.degree. C. or 20.degree. C. The total progressive motility (TPM) and the acrosome status of the spermatozoa were evaluated prior to sorting and at 0, 2, 12, 24, 36 and 48 h after sorting. The TPM was evaluated microscopically and acrosomes stained with FITC-PNA (Sigma-Aldrich) and classified as intact, patchy or lost. The effect of stallions, time and storage temperatures were analyzed using the Proc GLM procedure and least means comparisons made (SAS Institute).

There was an effect of stallion (p=0.03) on sperm motility and on the proportion of intact acrosomes over time. Staining and incubating the spermatozoa with Hoechst 33342 resulted in a decrease in the proportion of intact acrosomes (Table 1). However, the proportion of intact acrosomes observed after sorting was higher than in the sperm population prior to sorting. The proportion of intact acrosomes declined (p<0.0001) as the lost acrosomes increased (p<0.0001) during 48 h after sorting, but there was no effect of time on the proportion of patchy acrosomes. There was a significant effect of sperm storage temperature after sorting such that that storage for 12 h at 20.degree. C. resulted in higher motility than storage at 4.degree. C. Sex-sorting spermatozoa by flow cytometry results in the selection of a population of spermatozoa which can maintain acrosome integrity for 24 h, equivalent to fresh spermatozoa. The maintenance of sperm longevity for 12 h after FACS separation should enable sex-sorted spermatozoa to be shipped to mares located some distance from the site of the flow cytometer. TABLE-US-00005 TABLE 1 The motility and acrosome status of flow sorted spermatozoa over time. Stage of Processing TPM Acrosome intact Prestain 50.7.+−. 10.2 57.1.+−. 28.2 Post stain 42.0.+−. 17.1 42.3.+−. 26.7 Post incubation 48.0.+−. 15.7 34.9.+−. 27.1.sup.a 0 h Post sort 49.9.+−. 18.3 60.2.+−. 22.3.sup.b 2 h 4.degree. C. 34.3.+−. 19.3 47.1.+−. 28.3 20.degree. C. 40.8.+−. 21.8 53.9.+−. 24.5 12 h 4.degree. C. 8.5.+−. 12.8.sup.a 59.8.+−. 19.7 20.degree. C. 27.0.+−. 21.0.sup.b 66.6.+−. 12.0 24 h 4.degree. C. 4.8.+−. 12.9 56.2.+−. 16.8 20.degree. C. 17.2.+−. 17.9 64.3.+−. 16.4 48 h 4.degree. C. 0.0.+−. 0.0 32.7.+−. 25.0 20.degree. C. 5.1.+−. 8.6 41.6.+−. 24.0.sup.a,bValues within a column with different superscripts are significantly different (p<0.05).

Foals of predetermined sex have been accurately and reliably produced in a research setting (Lindsey et al., Equine Vet. J. 2002, 34: 128-132). Sex-sorted sperm would be more efficiently utilized by the industry, however, if frozen/thawed sex-sorted sperm were available. The objective of this study was to compare the motion characteristics of sperm that had been stored for 18 h at 15.degree. C., flow-sorted, and then frozen, to sperm that had been cryopreserved immediately following shipment at 18 h at 15.degree. C. Two ejaculates were used from each of five stallions. Following collection, sperm for both treatments were extended to 25.times.10.sup.6/mL in a Kenney+Modified Tyrodes (KMT) medium and stored in a water bath at 15.degree. C. for 18 h. After storage, sperm were allowed to reach ambient temperature (.about.22.degree. C.) prior to centrifugation at 600 g for 10 min. Seminal plasma was removed and the sperm pellet resuspended to 500.times.10.sup.6/ml in KMT. An aliquot of sperm was removed (Control) from this sample, extended to 87.times.10.sup.6/ml in a skin-mild, egg yolk freezing extended (4% glycerol; FR5), and allowed to slow cool to 5.degree. C. for 90 min before freezing in liquid nitrogen vapor. A second aliquot (Flow-sorted) of sperm was extended to 100.times.10.sup.6/ml in KMT, stained with Hoechst 33342 (5 mg/ml, Sigma-Aldrich, St. Louis Mo.), incubated for 30 minutes, and subsequently sorted by flow-cytometry. Sorted sperm was centrifuged at 850 g for 20 min, resuspended to 87.times.10.sup.6/ml in FR5, and allowed to cool slowly to 5.degree. C. for 90 min prior to cryopreservation. Sperm for both treatments were packaged in 0.25-ml straws, and each straw contained 20 million sperm. Sperm were evaluated (blindly) for visual progressive motility (2 observers) at 30 and 90 min post-thaw. An aliquot of sperm from each straw was diluted in both KMT and in KMT containing 2 mM caffeine. Samples were allowed to equilibrate for 5-10 min at 37.degree. C. prior to evaluation. A second straw of each treatment was evaluated (with and without caffeine) using the Hamilton-Thom Motility Analyzer (CASA). Results are in Table 1. Differences in motion parameters were determined by ANOVA. According to most measured responses, flow-sorting was detrimental to sperm motility. Additionally, 2 mM caffeine improved many sperm responses. There was an interaction whereby caffeine improved some responses more for sorted sperm than for control sperm. Therefore, the damage caused by sorting can be partially compensated for by caffeine. It is possible that similar compensation may occur in the mare reproductive tract Studies are currently in progress to compare the fertility of stored, cryopreserved stallion sperm to that of sperm that has been stored and sorted prior to cryopreservation. TABLE-US-00006 Vis Vis CASA CASA Treatment 30 90 Tot Prog VAP VSL VCL ALH BCF STR LIN C-Control 50.sup.a 47.sup.a 64.sup.a 60.sup.a 94.sup.a 80.sup.a 164.sup.a 6.19.sup.a 33.sup.a 83.sup.a 50.sup.a Control 45.sup.a 40.sup.b 50.sup.b 44.sup.b 82.sup.a 69.sup.a 144.sup.a 5.73.sup.a 33.sup.a 82.sup.a 50.sup.a C-Sorted 32.sup.b 31.sup.c 32.sup.c 21.sup.c 48.sup.b 38.sup.b 98.sup.b 4.75.sup.b 41.sup.b 73.sup.b 39.sup.b Sorted 18.sup.c 16.sup.d 24.sup.d 12.sup.d 39.sup.b 30.sup.b 80.sup.b 4.51.sup.b 37.sup.c 69.sup.b 38.sup.b .sup.a,b,c,dValues in the same column without common superscripts differ (P, 0.05). C-treatments stimulated with 2 mM caffeine.

Cow elk 3-6-yr of age in Colorado and Minnesota were synchronized for estrus in September by insertion of a progesterone CIDR into the vagina for 12-14 d. Upon removal of the CIDR, 200 IU of eCG was administered intramuscular and elk were timed-inseminated 60 h later. Fresh semen was collected via electro-ejaculation from a 5-yr old bull elk and slowly cooled over 4 h to about 20°C. for transportation as a neat ejaculate to the sperm-sorting laboratory. The ejaculate was concentrated to $1 \times 10^9$ sperm/ml for straining by centrifuging 1.5 ml aliquots for 10 sec at $15,000 \times g$. Semen was incubated in 112 $\mu$M Hoechst 33342 at $200 \times 10^6$ sperm/ml in a TALP medium for 45 min at 34°C., and then diluted to $100 \times 10^6$/ml for sorting. Sperm were sorted on the basis of differing DNA content of X and Y chromosome-bearing sperm. X chromosome-bearing elk sperm contained 3.8% more DNA than Y chromosome-bearing sperm. Sperm were flow-sorted over a 4 h period using MoFlo®SX operating at 50 psi with a TRIS-based sheath fluid. The 351 and 364 bands of an argon laser, emitting 150 mW, excited Hoechst 33342 dye bound to DNA. Both X and Y chromosome-bearing sperm were collected (about 92% purity as verified by reanalyzing sonicated sperm aliquots for DNA) were collected at about 4,700 sperm/sec into tubes containing 2 ml of 20% egg yolk-TRIS extender. Sorted volumes of 15 ml were sequentially collected. Approximately $110 \times 10^6$ sperm of each sex were sorted and cooled to 5°C. over 90 min. An equal volume of glycerol (12%) containing extender was added to the sorted volume at 5°C. Sorted sperm aliquots containing 30-ml were concentrated by centrifugation at 4°C. for 20 min at $850 \times g$. Sperm pellets were pooled, adjusted to $21.7 \times 10^6$ sperm/ml and loaded into 0.25-ml straws. Each straw, containing $5 \times 10^6$ total sperm, was frozen in liquid nitrogen vapor. As a control, $5 \times 10^6$ total sperm from the same ejaculate were frozen in 0.25 ml straws at the same time as the sexed sperm. After thawing for 30 sec at 37°C., 65% and 60% of sperm (control and sexed, respectively) were progressively motile as determined by visual estimates. Cows at 3 different locations and management schemes were inseminated using routine trans-cervical semen deposition in the uterine body. Pregnancy was determined 40-d post insemination by assaying blood for Pregnancy-Specific Protein B (Bio Tracking, Moscow, Id.). Ten cows at one location were in poor condition at the time of insemination and no pregnancies were achieved with sexed or control sperm. The pregnancy rate at the other locations with sexed sperm (61%; 11/18) was similar to that for control inseminates (50%; 3/6). These pregnancy rates (sexed and controls) resulted from fewer sperm than are used in normal elk artificial insemination. Nine of eleven (82%) of sexed calves were of the predicted sex.

The invention can further include a mammal produced in accordance with any of the above described embodiments of the invention, or can include a mammal of predetermined sex in accordance with the various embodiments of the invention that provide sperm cell insemination samples having an enriched population of either X-chromosome bearing sperm cells or enriched population of Y-chromosome bearing sperm cells, or a mammal produced in accordance with any embodiment of the invention in which a sperm cell insemination sample containing a low number of sperm cells compared to the typical number used to inseminate that particular species of mammal is used, or elk progeny produced in accordance with the invention as described above.

As can be easily understood from the foregoing, the basic concepts of the present invention may be embodied in a variety of ways. It involves both a sperm cell process system including both techniques as well as devices to accomplish sperm cell processing. In this application, various sperm cell processing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this nonprovisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which will be included in a full patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "flow-sorter" should be understood to encompass disclosure of the act of "flow-sorting"—whether explicitly discussed or not—and, conversely, were there effectively disclosure of the act of "flow-sorting", such a disclosure should be understood to encompass disclosure of a "flow-sorter" and even a "means for flow-sorting" Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the sperm cell processing devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, x) the various combinations and permutations of each of the elements disclosed, and xi) each potentially dependent claim or concept as a dependency on each and every one of the independent claims or concepts presented. In this regard it should be understood that for practical reasons and so as to avoid adding potentially hundreds of claims, the applicant may eventually present claims with initial dependencies only. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

The invention claimed is:

1. A method of modifying a sperm cell sample, comprising:
   a) obtaining said sperm cell sample;
   b) generating a fluid pressure;
   c) adjusting said fluid pressure to a pressure capable of modifying at least one fertility characteristic of said sperm cell sample;
   d) exposing said sperm cell sample of a) to said fluid pressure of c); and
   e) collecting said sperm cell sample after said exposing d), said sperm cell sample having a controlled modification of said at least one fertility characteristic.

2. The method of claim 1, wherein said adjusting said fluid pressure occurs in a range of about 20 psi (0.098 kg/cm$^2$) and about 100 psi (7.03 kg/cm$^2$).

3. The method as described in claim 2, wherein said adjusting said fluid pressure occurs between about 30 psi (2.10 kg/cm$^2$) and about 40 psi (2.81 kg/cm$^2$).

4. The method as described in claim 3, wherein said adjusting said fluid pressure of step c) further comprises incrementally adjusting said fluid pressure to modify said at least one fertility characteristic of said sperm cell sample.

5. The method as described in claim 4, wherein said at least one fertility characteristic is selected from the group consisting of: sperm cell motility, sperm cell viability, oocyte cleavage rate, blastocyst formation rate, pregnancy rate, and a combination thereof.

6. The method as described in claim 3, wherein said fluid pressure is selected from the group consisting of: about 30 psi when said at least one fertility characteristic comprises sperm cell motility; about 40 psi when said at least one fertility characteristic comprises sperm cell motility; about 30 psi when said at least one fertility characteristic comprises sperm cell viability; about 40 psi when said at least one fertility characteristic comprises sperm cell viability; about 40 psi when said at least one fertility characteristic comprises oocyte cleavage rate; about 40 psi when said at least one fertility characteristic comprises blastocyst formation rate; and about 40 psi when said at least one fertility characteristic comprises pregnancy rate.

7. The method of claim 1, wherein said fluid pressure generates a fluid stream having a fluid stream pressure.

8. The method of claim 7, further comprising generating said fluid stream within a conduit to provide said fluid stream pressure.

9. The method of claim 8, further comprising surrounding said fluid stream with a sheath fluid stream.

10. The method of claim 9, wherein said sheath fluid stream includes a sheath fluid selected from the group consisting of: a phosphate buffered saline (PBS), a citrate buffer, a 2.9% sodium citrate buffer, a HEPES buffer, a TRIS-based sheath fluid, and a combination thereof.

11. The method of claim 1, further comprising analyzing said sperm cells to discriminate between X-chromosome bearing sperm cells and Y-chromosome bearing sperm cells.

12. The method of claim 11, further comprising separating said X-chromosome bearing sperm cells from said Y-chromosome bearing sperm cells prior to said collecting.

13. A method of claim 12, wherein said sperm cell sample is selected from the group consisting of: a bovine sperm cell sample, an equine sperm cell sample, an ovine sperm cell sample, a canine sperm cell sample, a feline sperm cell sample, a swine sperm cell sample, a marine mammal sperm cell sample, a deer sperm cell sample, a primate sperm cell sample, a goat sperm cell sample, and a combination thereof.

14. The method of claim 12, further comprising isolating said X-chromosome bearing sperm cells or said Y-chromosome bearing sperm cells as sex selected sperm samples, and further comprising fertilizing oocytes with said sex selected sperm samples by in-vitro fertilization.

* * * * *

UNITED STATES PATENT AND TRADEMARK OFFICE
CERTIFICATE OF CORRECTION

| | |
|---|---|
| PATENT NO. | : 8,765,365 B2 |
| APPLICATION NO. | : 13/953372 |
| DATED | : July 1, 2014 |
| INVENTOR(S) | : John L. Schenk, George E. Seidel and Tae Kwang Suh |

It is certified that error appears in the above-identified patent and that said Letters Patent is hereby corrected as shown below:

Title Page, Item (57) in the Abstract:

Line 1: "A sperm cell process system providing to generate sperm cell insemination samples"
should read --A sperm cell process system for the production of sperm cell insemination samples--.

Signed and Sealed this
Twelfth Day of April, 2016

Michelle K. Lee
*Director of the United States Patent and Trademark Office*